United States Patent [19]

Volpenhein

[11] Patent Number: 4,518,772

[45] Date of Patent: May 21, 1985

[54] SYNTHESIS OF HIGHER POLYOL FATTY ACID POLYESTERS USING HIGH SOAP:POLYOL RATIOS

[75] Inventor: Robert A. Volpenhein, Cincinnati, Ohio

[73] Assignee: The Proctor & Gamble Company, Cincinnati, Ohio

[21] Appl. No.: 507,826

[22] Filed: Jun. 23, 1983

[51] Int. Cl.$^3$ .............................................. C07H 1/00
[52] U.S. Cl. .................. 536/119; 260/410.6; 536/124
[58] Field of Search ...................... 536/119; 260/410.6

[56] References Cited

U.S. PATENT DOCUMENTS

| | | | |
|---|---|---|---|
| 2,893,990 | 7/1959 | Hass et al. | 536/119 |
| 3,251,827 | 5/1966 | Schnell et al. | 536/119 |
| 3,558,597 | 1/1971 | von Brachel et al. | 536/119 |
| 3,963,699 | 6/1976 | Rizzi et al. | 536/119 |
| 3,996,206 | 12/1976 | Parker et al. | 536/119 |
| 4,032,702 | 6/1977 | James | 536/119 |
| 4,334,061 | 6/1982 | Brossier | 536/119 |

OTHER PUBLICATIONS

Rizzi and Taylor, *Journal of the American Oil Chemists' Society*, 55:398, (1978).

*Primary Examiner*—Johnnie R. Brown
*Attorney, Agent, or Firm*—Steven J. Goldstein; Jack D. Schaeffer; Richard C. Witte

[57] ABSTRACT

An improved solvent-free transesterification process for producing higher polyol fatty acid polyesters is disclosed. In this process a mixture of a polyol, a fatty acid methyl, 2-methoxy ethyl or benzyl ester, an alkali metal fatty acid soap, and a basic catalyst, having a molar ratio of soap:polyol of from about 0.6:1 to about 1:1, preferably from about 0.75:1 to about 1:1, is heated to form a homogeneous melt. To this melt is subsequently added excess fatty acid methyl, 2-methoxy ethyl or benzyl ester, yielding the desired polyol fatty acid polyesters.

18 Claims, No Drawings

SYNTHESIS OF HIGHER POLYOL FATTY ACID POLYESTERS USING HIGH SOAP:POLYOL RATIOS

TECHNICAL FIELD

This invention relates to an improved, high yield synthesis of higher polyol fatty acid polyesters, sucrose polyesters in particular, via transesterification.

BACKGROUND OF THE INVENTION

The food and pharmaceutical industries have recently focused attention on polyol polyesters for use as low calorie fats in food products and as pharmaceutical agents, e.g., for the lowering of blood cholesterol levels. U.S. Pat. No. 3,600,186, Mattson and Volpenhein, issued Aug. 17, 1971, describes low calorie food compositions formed by replacing at least a portion of the fat content of food products with higher polyol fatty acid polyesters. U.S. Pat. No. 3,954,976, Mattson and Volpenhein, issued May 4, 1976, describes pharmaceutical compositions for inhibiting the absorption of cholesterol comprising effective unit dosage amounts of higher polyol fatty acid polyesters, as well as the method for treating hypercholesterolemia using these polyesters. Additional pharmaceutical uses are described in U.S. Pat. No. 4,241,054, Volpenhein and Jandacek, issued Dec. 23, 1980 (removal of halogenated toxins from the body), and U.S. Pat. No. 4,264,583, Jandacek, April 28, 1981 (treatment of gallstones).

As a result of these many uses for the higher polyol fatty acid polyesters, it would be desirable to have an efficient high yield synthesis for them. Historically, such syntheses have been conducted using a mutual solvent to solubilize a polyol and esters of long chain fatty acids, thus providing a homogeneous reaction medium suitable for catalytic transesterification. One variation of this process, known as the Snell synthesis, has been employed as a means for preparing both poly- and lower esters. However, the solvents employed in such processes are difficult to separate from the final product and are characteristically toxic, therefore limiting the usefulness of such syntheses in the food and pharmaceutical industries. Accordingly, efforts have been directed toward the discovery of high yield syntheses of polyol fatty acid polyesters which do not employ toxic solvents.

BACKGROUND ART

U.S. Pat. No. 3,963,699, Rizzi and Taylor, issued June 15, 1976, describes the basic solvent-free transesterification process for synthesizing higher polyol fatty acid polyesters. In this three-step reaction, a mixture of a polyol (such as sucrose), a fatty acid lower alkyl ester (such as fatty acid methyl ester), an alkali metal fatty acid soap, and a basic catalyst is heated, forming a homogeneous melt, to which is added excess fatty acid lower alkyl ester to form the higher polyol fatty acid polyesters. The polyesters are then separated from the reaction mixture. The catalysts described in this patent as being useful include alkali metals, alloys of two or more alkali metals, alkali metal hydrides, and alkali metal alkoxides. The processes exemplified in this patent utilize sodium hydride, sodium hydroxide or dispersions of potassium as catalysts, and soap:sucrose mole ratios of about 0.3–0.4:1.

Rizzi and Taylor, *Journal of the American Oil Chemists' Society* 55:398 (1978), further describe the reaction set forth in the above-referenced Rizzi and Taylor patent. Advantages are demonstrated for catalyzed reactions versus uncatalyzed reactions; sodium hydride and sodium-potassium alloy are taught to be effective catalysts. At page 400, the paper teaches that alkali metal carbonates and alkali metal alkoxides are relatively ineffective as catalysts.

U.S. Pat. No. 4,334,061, Brossier, III, issued June 8, 1982, describes a method for separating and purifying the polyesters formed by the Rizzi and Taylor process. The procedure requires, in the separation step, an alkaline pH which is obtained by adding an alkali metal carbonate to the reaction mixture at the conclusion of the transesterification reaction. Thus, the carbonate compounds added do not function as catalysts for the transesterification reaction.

U.S. Pat. No. 2,893,990, Hass, et al, issued July 7, 1959, describes a process for making carboxylic acid lower esters of sucrose and raffinose; generally, mono- or diesters are formed. In the process, a non-sucrose ester of a fatty acid (e.g., methyl stearate or methyl palmitate) is reacted with sucrose, preferably in a solvent. A wide range of alkaline catalysts, including sodium carbonate and potassium carbonate, are disclosed for use in the reaction.

It has now been found that by modifying the solvent-free transesterfication reaction described in the Rizzi and Taylor patent, discussed above, using potassium carbonate, sodium carbonate or barium carbonate as the catalyst and/or using significantly higher soap:sucrose mole ratios than those originally envisioned, shorter reaction times, more complete utilization of the polyol component, and improved yields of the higher polyol polyesters can be obtained.

It is, therefore, an object of this invention to provide an improved solvent-free high yield synthesis of polyol fatty acid polyesters.

SUMMARY OF THE INVENTION

The present invention encompasses an improved solvent-free transesterification process for synthesizing higher polyol fatty acid polyesters comprising the steps of:

(1) heating a mixture of (a) a polyol selected from the group consisting of monosaccharides, disaccharides and sugar alcohols, (b) a fatty acid ester selected from the group consisting of methyl esters, 2-methoxy ethyl esters, benzyl esters and mixtures thereof, (c) an alkali metal fatty acid soap, and (d) a basic catalyst, to a temperature of from about 110° C. to about 180° C. at a pressure of from about 0.1 mm to about 760 mm of mercury to form a homogenous melt; and (2) subsequently adding to the reaction product of step (1) excess fatty acid ester selected from the group consisting of methyl esters, 2-methoxy ethyl esters, benzyl esters and mixtures thereof;

the improvement being obtained by using molar ratios of soap:polyol in step (1) of from about 0.6:1 to about 1:1, preferably from about 0.75:1 to about 1:1, more preferably from about 0.75:1 to about 0.85:1, most preferably about 0.75:1.

DETAILED DESCRIPTION OF THE INVENTION

The present invention encompasses improvements in the solvent-free transesterification reaction for forming higher polyol fatty acid polyesters described and claimed in U.S. Pat. No. 3,963,699, Rizzi and Taylor, issued June 15, 1976, incorporated herein by reference. This process is characterized by a three-step reaction procedure, summarized below. By utilizing the improvements taught herein, the reaction described in the Rizzi and Taylor patent can be improved by reducing excessive foaming, shortening reaction times, increasing the yields of the higher polyol fatty acid polyesters, and yielding products having better (lighter) color characteristics. In fact, the improvements herein permit the reaction to be formulated as a single step solvent-free reaction for the production of higher polyol fatty acid polyesters.

STEP 1

In the first step of the present process, a heterogeneous mixture of a polyol, fatty acid methyl, 2-methoxy ethyl or benzyl esters, an alkali metal fatty acid soap, and a basic catalyst is reacted to form a homogeneous melt comprising partially esterified polyol and unreacted starting materials.

As used herein, the term "polyol" is intended to include any aliphatic or aromatic compound containing at least two free hydroxyl groups. In practicing the process disclosed herein, the selection of a suitable polyol is simply a matter of choice. For example, suitable polyols may be selected from the following classes: saturated and unsaturated straight and branched chain linear aliphatics; saturated and unsaturated cyclic aliphatics, including heterocyclic aliphatics; or mononuclear or polynuclear aromatics, including heterocyclic aromatics. Carbohydrates and non-toxic glycols are preferred polyols. Monosaccharides suitable for use herein include, for example, mannose, galactose, arabinose, xylose, ribose, apiose, rhamnose, psicose, fructose, sorbose, tagitose, ribulose, xylulose, and erythrulose. Oligosaccharides suitable for use herein include, for example, maltose, kojibiose, nigerose, cellobiose, lactose, melibiose, gentiobiose, turanose, rutinose, trehalose, sucrose and raffinose. Polysaccharides suitable for use herein include, for example, amylose, glycogen, cellulose, chitin, inulin, agarose, zylans, mannan and galactans. Although sugar alcohols are not carbohydrates in a strict sense, the naturally occurring sugar alcohols are so closely related to the carbohydrates that they are also preferred for use herein. The sugar alcohols most widely distributed in nature and suitable for use herein are sorbitol, mannitol and galactitol.

Particularly preferred classes of materials suitable for use herein include the monosaccharides, the disaccharides and sugar alcohols. Preferred carbohydrates and sugar alcohols include xylitol, sorbitol and sucrose.

As used herein, the term "fatty acid esters" is intended to include the methyl, 2-methoxy ethyl and benzyl esters of fatty acids containing about eight or more carbon atoms, and mixtures of such esters. Suitable esters can be prepared by the reaction of diazoalkanes and fatty acids, or derived by alcoholysis from the fatty acids naturally occurring in fats and oils. Suitable fatty acid esters can be derived from either saturated or unsaturated fatty acids. Suitable preferred saturated fatty acids include, for example, capric, lauric, palmitic, stearic, behenic, isomyristic, isomargaric, myristic, caprylic, and anteisoarachadic. Suitable preferred unsaturated fatty acids include, for example, maleic, linoleic, licanic, oleic, linolenic, and erythrogenic acids. Mixtures of fatty acids derived from soybean oil, palm oil, sunflower oil, safflower oil, and corn oil are especially preferred for use herein. Methyl esters are the preferred fatty acid esters for use herein, since their use in the process herein tends to result in unusually high yields of polyol fatty acid polyesters.

As used herein, the term "alkali metal fatty acid soap" is intended to include the alkali metal salts of saturated and unsaturated fatty acids having from about eight to about eighteen carbon atoms. Accordingly, suitable alkali metal fatty acid soaps include, for example, the lithium, sodium, potassium, rubidium, and cesium salts of fatty acids such as capric, lauric, myristic, palmitic, licanic, parinaric, and stearic acids, as well as mixtures thereof. Mixtures of fatty acids derived from soybean oil, sunflower oil, safflower oil, and corn oil are preferred for use herein. Accordingly, preferred alkali metal fatty acid soaps include, for example, the potassium soap made from soybean oil fatty acids and the sodium soap made from sunflower oil fatty acids.

The basic catalysts generally suitable for use herein are those selected from the group consisting of alkali metals, such as sodium, lithium and potassium; alloys of two or more alkali metals, such as sodium-lithium and sodium-potassium alloys; alkali metal hydrides, such as sodium, lithium and potassium hydride; and alkali metal alkoxides, such as potassium t-butoxide and sodium methoxide.

In a particularly preferred embodiment of the present invention, the basic catalyst used in the reaction is potassium carbonate, sodium carbonate, barium carbonate, or mixtures of these compounds. It has been found that when these specific compounds are used as the catalyst, shorter reaction times and/or increased yields of the higher polyol polyesters are obtained when compared to essentially identical reactions carried out using more conventional catalysts, such as sodium hydride, potassium hydride, soap, or sodium methoxide. These preferred catalysts may also be used in admixture with the more conventional basic catalysts, described above. Potassium carbonate is the most preferred catalyst for use herein. The use of these catalysts is further disclosed and claimed in concurrently-filed patent application Ser. No. 507,825, Volpenhein, Synthesis of Higher Polyol Fatty Acid Polyesters using Carbonate Catalysts, incorporated herein by reference.

In a preferred embodiment of this invention, the catalyst is dispersed in a suitable carrier so as to insure uniform distribution of the catalyst throughout the reaction mass. Suitable carriers or dispersing agents include, for example, methanol and fatty acid methyl esters.

In carrying out step 1, the above-described reactants are combined to form a heterogeneous mixture. The precise ratio of reactants can be freely selected from within the guidelines set forth hereinafter. However, routine experimentation may be necessary in order to establish the optimum concentrations for a given set of reactants. In general, the heterogeneous mixture comprises from about 10% to about 50%, preferably from about 15% to about 30%, by weight of the polyol; from about 40% to about 80%, preferably from about 55% to about 75%, by weight of the fatty acid esters; from about 1% to about 30%, preferably from about 5% to about 20%, by weight of the alkali metal fatty acid soap; and about from about 0.05% to about 5%, preferably from about 0.1% to about 0.5%, by weight of the basic catalyst component.

It has surprisingly been found that when this mixture is formed so as to include relatively high molar ratios of soap:polyol, increased yields of the higher polyesters (e.g., the octaesters) are obtained when compared with similar reactions carried out using lower artdisclosed soap:polyol molar ratios (e.g., about 0.3–0.4:1). Specifically, these higher soap:polyol ratios result in increased yields of the higher polyols, more complete utilization of the polyol reaction component, and/or faster disappearance of free polyol from the reaction mixture. Soap:polyol molar ratios in step 1 of from about 0.6:1 to 1:1 are, therefore, preferred for use in the present invention. More preferred soap:polyol ratios fall in the range from about 0.75:1 to about 1:1, from about 0.75:1 to about 0.85:1, and most preferably about 0.75:1.

The heterogeneous mixture is heated to a temperature within the range of from about 110° C. to about 180° C., preferably from about 130° C. to about 145° C., under a pressure of from about 0.1 mm to about 760 mm, preferably from about 0.5 mm to about 25 mm, of mercury. Within these temperature and pressure ranges, a homogeneous melt of partially esterified polyol and unreacted starting materials will form in from about 1 to 4 hours.

STEP 2

In the second step of the instant process, excess fatty acid methyl, 2-methoxy ethyl, or benzyl esters are added to the homogeneous melt formed in step 1. As used herein, the term "excess" is intended to include sufficient fatty acid esters to raise the overall ester:polyol mole ratio above about 8:1, preferably to about 12:1. Although ratios beyond 12:1 can be used, as a general rule, such ratios do not noticeably decrease reaction time or improve the yield and, therefore, tend to be impractical. When fatty acid methyl esters are used, it is preferred that after the excess ester is added to the reaction mixture, the mixture be heated to a temperature of from about 120° C. to about 160° C., preferably about 135° C., at a pressure from about 0.1 mm to about 10 mm, preferably from about 0.5 mm to about 2 mm, of mercury to form the polyol fatty acid polyester material. The reaction time for step 2 is preferably less than about 10 hours, and generally is between about 2 and 8 hours.

It should be noted that as the transesterification reaction proceeds, a lower alcohol is formed as a byproduct. In order to promote the reaction, the alcohol by-product is preferably removed. Many removal techniques are known in the art, any one of which can be used to effectively and efficiently remove the lower alcohol. Vacuum removal both with and without an inert gas sparging has been found to promote the reaction. In any event, the formation of a lower alcohol presents no significant obstacle to the use of the process in the food or pharmaceutical industries.

The use of the preferred catalysts and soap:polyol ratios, defined herein, permit the combination of steps 1 and 2 into a single reaction step. In this single step approach, a mixture of (a) a polyol selected from monosaccharides, disaccharides and sugar alcohols; (b) an alkali metal fatty acid soap; (c) a basic catalyst selected from potassium carbonate, sodium carbonate and barium carbonate; and (d) an excess of fatty acid methyl, 2-methoxy ethyl or benzyl ester (wherein the soap:polyol molar ratio is from about 0.6:1 to about 1:1, preferably from about 0.75:1 to about 1:1, more preferably from about 0.75:1 to about 0.85:1, most preferably about 0.75:1), is heated to a temperature of from about 100° C. to about 180° C. at a pressure of from about 0.1 mm to about 760 mm of mercury, thereby forming higher polyol fatty acid polyesters.

STEP 3

In the third step of the process, the polyol fatty acid polyesters formed in step 2 are separated from the reaction mix containing polyesters, soap, and unreacted starting materials. Separation can be accomplished by any of the separation procedures routinely used in the art. Distillation, water washing, conventional refining techniques or solvent extraction are preferred due to their simplicity and economy.

The following non-limiting examples are intended to further clarify the invention, but should not be construed as limiting thereof.

Each of the following reactions was carried out in a 1 liter 3-neck flask containing a stirrer, thermometer, reflux condensor, and vacuum outlet.

EXAMPLE I

Two Stage Reaction

Step (1): 3.6 g 85% KOH pellets (0.055 moles) dissolved in some methanol and 103 g (0.347 moles) soybean oil fatty acid methyl esters (FAME) were heated and stirred at reflux for two hours. 25 g sucrose (0.073 moles) and 1 g potassium carbonate were added and the condensor removed. The soap:sucrose molar ratio of the mixture was 0.75:1. The methanol was evaporated from the mixture under a gentle stream of nitrogen. When the reaction reached 100° C., a vacuum was applied and the temperature brought to 135° C. Conditions were maintained for two hours.

Step (2): 174 g additional FAME (0.585 moles) was drawn into the reactor. The final molar ratio of FAME to sucrose was 12:1. The temperature was allowed to recover to 135° C. and stirring under vacuum was continued for three hours. The vacuum slowly decreased in this time to from 5.0 to 0.5 mm Hg, as the methanol formed during the reactions was removed.

The reaction was cooled to 90°–100° C. and 200 ml 80:20:2 (by weight) water:alcohol:salt added and the mix stirred for 10 minutes at 80° C. The reaction mix was transferred to a separatory funnel and the phases allowed to separate. The lower aqueous soap solution was discarded and the lipid phase returned to the reactor for additional washes: first with a second 80:20:2 water: alcohol:salt wash and then with 2% aqueous acetic acid and two water washes (all at 80° C.). The lipid was dried under vacuum, bleached with 1–5% Filtrol 105 (a bleaching earth), filtered and steam deodorized at 205° C. to remove excess FAME. The sample was weighed and the yield calculated as percent sucrose recovered as octaester.

The octaester content of the reaction product was determined by separating the mix on a silica gel column and weighing the relative amount of octaester and partial esters recovered. The product formed comprised a mixture of the higher polyesters of sucrose, having a high octaester content.

Substantially similar results are obtained when the potassium carbonate catalyst is replaced, in whole or in part, by sodium carbonate, barium carbonate or mixtures thereof. Similar results are also obtained when the sucrose is replaced, in whole or in part, by sorbitol, xylitol, mannitol or galactitol. The FAME is replaced, in whole or in part, with soybean oil benzyl esters, soybean oil 2-methoxy ethyl esters or the methyl esters of palm oil, sunflower oil, safflower oil, or corn oil; similar results are obtained. Similar results are also obtained when the potassium soybean oil fatty acid soaps used in the above example are replaced, in whole or in part, by the lithium, sodium, rubidium or cesium salts of fatty acids derived from sunflower oil, safflower oil or corn oil.

EXAMPLE II

Single Stage Reaction 3.6 g 85% KOH pellets (0.055 moles) dissolved in 50 ml methanol and 278 g (0.933 moles) soybean oil fatty acid methyl esters were refluxed for two hours. 25 g (0.073 moles) sucrose and 1 g potassium carbonate were added. The soap:sucrose molar ratio of the mixture was 0.75:1. The methanol was evaporated from the mixture under nitrogen. When the reaction reached 100° C., a vacuum was applied and the temperature raised to 135° C. Reaction conditions were maintained for four hours. The reaction was cooled, 15 ml. of water added, stirred 5 minutes and certrifuged (45 minutes, 8000 RPM). The mixture of higher sucrose polyesters was then decanted from the soap. The mixture was then bleached with 1–5% Filtrol 105, filtered and steam deodorized at 205° C. to remove excess FAME.

The product formed comprised a mixture of the higher polyesters of sucrose, having a high (about 85%) octaester content.

Substantially similar results are obtained when the potassium carbonate catalyst is replaced, in whole or in part, by sodium carbonate or barium carbonate. Similar results are also obtained when the sucrose is replaced, in whole or in part, by sorbitol, xylitol, mannitol or galactitol. The FAME is replaced, in whole or in part, with soybean oil benzyl esters, soybean oil 2-methoxy ethyl esters or the methyl esters of palm oil, sunflower oil, safflower oil, or corn oil; similar results are obtained. Similar results are also obtained when the potassium soybean oil fatty acid soaps used in the above example are replaced, in whole or in part, by the lithium, sodium, rubidium or cesium salts of fatty acids derived from sunflower oil, safflower oil or corn oil.

EXAMPLE III

The general procedure described in Example I was used to compare the effectiveness of various catalysts. Those tested included potassium carbonate ($K_2CO_3$), sodium carbonate ($Na_2CO_3$), sodium methoxide (NaOMe), sodium hydride (Na.H) and potassium hydroxide (KOH), all at 10 mole percent of the sucrose in the reaction. $K_2CO_3$, NaOMe, and potassium hydride (K.H) were also compared at four weight percent of the sucrose. The results are summarized in the table below.

| Catalyst | Effect of Various Catalysts on the Synthesis of Sucrose Polyesters | | |
|---|---|---|---|
| | Concentration (Sucrose Basis) | % Yield | % Octa-Ester |
| $K_2CO_3$ | 10 mole % | 90 | 75 |
| Na.H | 10 mole % | 76 | 36 |
| NaOMe | 10 mole % | 85 | 63 |
| KOH | 10 mole % | 58 | Not determined |
| $Na_2CO_3$ | 10 mole % | 79 | 40 |
| None | — | 45 | 5 |
| $K_2CO_3$ | 4 weight % | 92 | 79 |
| NaOMe | 4 weight % | 79 | 79 |

| Catalyst | Effect of Various Catalysts on the Synthesis of Sucrose Polyesters | | |
|---|---|---|---|
| | Concentration (Sucrose Basis) | % Yield | % Octa-Ester |
| K.H | 4 weight % | 30 | 30 |

EXAMPLE IV

To assess the effect of soap level on the reaction, the reaction as described in Example I was utilized. The concentration of soap in the reaction mix was controlled by either varying the amount of KOH added at the beginning or by adding varying amounts of preformed potassium soaps.

Two analytical methods were used to monitor the effect of soap on the reaction. In the first, varying amounts of KOH and radiolabelled sucrose were used. At the end of the first two hours, before the second addition of FAME, the reaction was stopped and partitioned between hot water and ethyl acetate. The amount of $^{14}C$ activity found in the water relative to that added as free sucrose at the beginning of the reaction was a measure of unreacted sucrose. These results are summarized below.

| Effect of Soap Concentration On Sucrose Reaction | | |
|---|---|---|
| Grams KOH Added | Molar Ratio Soap:Sucrose | Unreacted Sucrose Remaining after 2 hrs. |
| 3.6 | 0.75 | 1.2 |
| 2.4 | 0.5 | 3.6 |
| 1.4 | 0.3 | 14.0 |
| 0 | 0 | 100 |

In the second test, varying amounts of pre-formed potassium soap were added to the mixture in place of KOH. The effect of the soap was judged by measuring yield of sucrose polyesters and octaester content. The results obtained are as follows.

| Effect of Soap Concentration On Yield of Sucrose Polyester | | | |
|---|---|---|---|
| Grams Potassium Soap Added | Molar Ratio Soap:Sucrose | % Yield | % Octaester |
| 4.7 | 0.2 | Foamed & charred too badly during reaction to recover | |
| 7.7 | 0.33 | 75 | 7 |
| 15.0 | 0.64 | 90 | 30 |
| 17.6 | 0.75 | 93 | — |
| 23.5 | 1.0 | 91 | 4 |

What is claimed is:

1. In a solvent-free transesterification process for synthesizing higher polyol fatty acid polyesters comprising the steps of:
   (1) heating a mixture of (a) a polyol selected from a group consisting of monosaccharides, disaccharides and sugar alcohols, (b) a fatty acid ester selected from the group consisting of methyl esters, 2-methoxy ethyl esters, benzyl esters, and mixtures thereof, (c) an alkali metal fatty acid soap, and (d) a basic catalyst, to a temperature of from about 110° C. to about 180° C. at a pressure of from about 0.1 mm to about 760 mm of mercury to form a homogeneous melt; and (2) subsequently adding to the reaction product of step (1) excess fatty acid ester selected from the group consisting of methyl esters, 2-methoxy ethyl esters, benzyl esters, and mixtures thereof;

the improvement wherein the molar ratio of soap:polyol in step (1) is from about 0.6:1 to about 1:1.

2. The process according to claim 1 wherein the molar ratio of soap:polyol is from about 0.75:1 to about 1:1.

3. The process according to claim 2 wherein the polyol is a disaccharide.

4. The process according to claim 2 wherein the polyol is selected from the group consisting of sucrose, xylitol, sorbitol, and mixtures thereof.

5. The process according to claim 2 wherein the fatty acid esters are fatty acid methyl esters.

6. The process according to claim 5 wherein the methyl esters are derived from materials selected from the group consisting of soybean oil, safflower oil, palm oil, sunflower oil, corn oil and mixtures thereof.

7. The process according to claim 2 wherein the mixture of step (1) is heated to a temperature of from about 130° C. to about 145° C.

8. The process according to claim 2 wherein the basic catalyst is selected from the group consisting of alkali metals, alloys of alkali metals, alkali metal hydrides, alkali metal alkoxides, and mixtures thereof.

9. The process according to claim 2 wherein the reaction mixture of step (1) comprises from about 10% to about 50% by weight of the polyol, from about 40% to about 80% by weight of the fatty acid ester, from about 1% to about 30% by weight of the alkali metal fatty acid soap, and from about 0.05% to about 5% by weight of the catalyst component.

10. The process according to claim 9 wherein the polyol is sucrose.

11. The process according to claim 10 wherein the fatty acid esters are fatty acid methyl esters.

12. The process according to claim 11 wherein the methyl esters are derived from a material selected from the group consisting of soybean oil, safflower oil, palm oil, sunflower oil, corn oil, and mixtures thereof.

13. The process according to claim 12 wherein the mixture of step (1) is heated to a temperature of from about 130° C. to about 145° C.

14. The process according to claim 13 wherein the catalyst is selected from the group consisting of alkali metals, alloys of alkali metals, alkali metal hydrides, alkali metal alkoxides, and mixtures thereof.

15. The process according to claim 14 wherein after the addition of the ester in step (2), the reaction mixture is heated to a temperature of from about 120° C. to about 160° C. at a pressure of from about 0.1 mm to about 10 mm of mercury to form the higher polyol fatty acid polyesters.

16. The process according to claim 14 wherein the molar ratio of soap:polyol in step (1) is from about 0.75:1 to about 0.85:1.

17. The process according to claim 16 wherein the molar ratio of soap:polyol in step (1) is about 0.75:1.

18. The process according to claim 9 wherein water is added to the mixture of step (2), said mixture is centrifuged and the higher polyol fatty acid polyesters are separated therefrom.

* * * * *